US005607434A

United States Patent [19]
Alvino

[11] Patent Number: 5,607,434
[45] Date of Patent: Mar. 4, 1997

[54] DEVICE FOR AND METHOD OF REMOVING TICKS

[76] Inventor: Joseph J. Alvino, P.O. Box 158, Newfield, N.J. 08344

[21] Appl. No.: 512,480

[22] Filed: Aug. 8, 1995

[51] Int. Cl.⁶ .................................................. A61B 17/50
[52] U.S. Cl. ............................ 606/131; 606/210; 30/124
[58] Field of Search ..................................... 606/131, 210, 606/138, 205, 206, 211; 294/100; 254/18; 81/300, 304, 3.44, 3.45; 30/124, 136, 137

[56]  References Cited

U.S. PATENT DOCUMENTS

| | | | |
|---|---|---|---|
| 2,302,810 | 2/1941 | Steegmuller | 30/124 |
| 4,494,542 | 1/1985 | Lee | 606/138 |
| 4,537,207 | 8/1985 | Gilhaus | 606/131 |
| 4,938,764 | 7/1990 | Glaberson | 606/131 |
| 5,116,347 | 5/1992 | Butler | 606/131 |
| 5,276,306 | 1/1994 | Huffman | 219/229 |
| 5,334,195 | 8/1994 | Gollobin | 606/131 |
| 5,447,511 | 9/1995 | Gadd | 606/131 |
| 5,466,456 | 11/1995 | Glover | 606/131 |

FOREIGN PATENT DOCUMENTS

| | | | |
|---|---|---|---|
| 406047684 | 7/1992 | Japan | 254/18 |
| 295557 | 8/1928 | United Kingdom | 30/136 |
| 2166681 | 5/1986 | United Kingdom | 254/18 |

*Primary Examiner*—Robert A. Hafer
*Assistant Examiner*—Justine Yu
*Attorney, Agent, or Firm*—Lennox & Murtha, P.A.

[57]  ABSTRACT

A tick removing device includes an upwardly angled fixed front end section with a V-shaped notch opening to the front with two blunt points. A bottom surface of the front end is slid along the skin of the host toward the embedded tick with a slight pressure sliding the opening of the V-shaped notch past the tick until the narrowing edges of the V-shaped notch contact the tick's body lifting the tick away from the flesh. The device includes a cup or a sticky patch to catch the removed tick.

11 Claims, 3 Drawing Sheets

5,607,434

DEVICE FOR AND METHOD OF REMOVING TICKS

BACKGROUND OF THE INVENTION

This invention is directed to a device and a method for removing ticks from domesticated animals and human beings. Ticks are common in woodlands and grasslands and are even found in the backyards of modern suburbia. Wild animals, particularly deer and mice are bitten and carry ticks spreading them over wide areas. Domesticated animals such as dogs and cats fall prey to the tick, which after grabbing hold of the new host, buries its head through the epidermis to feed on the blood of the host. During walks in woods or fields, persons, with or without an accompanying pet, may suddenly discover that a tick has imbedded itself someplace on the person's or the pet's body. Common pocket tools are of little help. It would be counter productive to use a knife or even tweezers to cut off the tick's body leaving the head imbedded under the skin. This would likely cause an infection. More careful use of tweezers to remove ticks is only marginally effective since it is not desirable to squeeze the body of the tick and risk forcing liquids from the inside of the tick into the person or the pet. It is difficult to grasp only the neck of the tick as it is hardly visible. The task of removing a tick from a pet is particularly difficult when the host animal is struggling in the hands of the person removing the tick. Carrying various chemicals and other equipment to coax the tick out of the skin is impractical, generally ineffective, at the least a bother, and are not easily used out in the woods. Chemicals that sting exacerbate the suffering of the animal.

The most common problem with ticks is the pet owner having to remove them from a struggling and, most times, uncooperative animal. Various devices have been provided to remove ticks from the body, but none satisfy the needs above nor attain the objects described herein below. These devices include a tick remover for people and animals in U.S. Pat. No. 5,116,347 to Butler. The Butler device brings two jaws together to grasp the neck of the tick and pull it free. As noted in the Butler specification, it is not desirable to squeeze the body of the tick. Some ticks, such as deer ticks, are small and with this type of device, it is difficult to avoid squeezing the body before removing the tick. Another tick removing device is described in U.S. Pat. No. 4,938,764 to Glaberson. This device utilizes a wire loop attached to a grasping handle. The loop is placed around the body of the tick and adjusted so that the loop fits on the tick's neck, after which the device is pulled away from the skin pulling the head of the tick from the host's body. Again, smaller ticks are more difficult to handle with this kind of device and the tick commonly ends up popping off to another part of the animal's body or to the ground making it difficult to relocate. Another device described in U.S. Pat. No. 5,276,306 to Huffman utilizes a hot needle which is used to pierce the tick. Devices for other uses include a device for removing splinters in U.S. Pat. No. 5,334,195 to Gollobin and a skin conditioning device described in U.S. Pat. No. 1,965,861 to Schneider.

SUMMARY OF INVENTION

It is an object of the protection sought to provide a device that is compact in size and immediately accessible for removing ticks from a body. The instrument is of a size that it may be carried in a pocket, pocketbook, or in a companion pouch.

It is a further object of the protection sought to provide an instrument that is simple to use and may be employed by adults, as well as older children with little risk of harm to the user or the host.

An additional object of the protection sought is to provide a tick removing device which is easily constructed, has no moving parts, and is economical to manufacture.

A further object of the protection sought is to provide a tick removing device that works on essentially all animals regardless of the length of the hair, fur, or thick flesh. It is easy to use the device and method of this invention without pulling the hair of the animal, thus minimizing discomfort of the animal.

It is a particular object of the invention sought to provide a tick removing device that can be operated with only one hand.

It is a further object of the protection sought to provide a tick removing device that easily lifts and holds the removed tick for transport to a place of disposal.

The tick removing device of the protection sought has an angled fixed front end. The angle extends upwardly and frontwardly from a plane of a rear end of the device that is grasped with the hand. A V-shaped notch is cut into the front end, which preferably terminates with two blunt points. The angling of the front end section of the instrument allows the rear section to be grasped and the bottom surface of the front end to be slid along the skin of the host toward the embedded tick. The bottom surface of the front section of the device is placed in contact with the skin close to the embedded tick. The device is moved forward with a slight pressure against the skin of the animal sliding the opening of the V-shaped notch past the tick until the narrowing edges of the V-shaped notch contact the tick's body. A slight continued sliding pressure against the tick lifts the tick away from the flesh. At no time will the person using the device need to touch the tick and incur essentially any risk of contracting a disease. The term "animal" as used in this specification and claims includes Homo Sapiens as well as domesticated animals.

An aspect of the invention is a tick removing device to lift off ticks that have penetrated an animal's skin. The device includes an integral elongate body that includes a top, bottom, a front end, and a rear end section shaped to be grasped in a hand of a person terminating in a rear end. The device further includes a front end section that includes a "V" shaped notch cut into the front end with a point of the notch extending towards the rear end and a wide portion of the notch opening through the front end. The front end section further includes a bottom face angled frontwardly and upwardly from a position located at or rearwardly of the point of the notch. The side edges of the notch proximate the point of the notch are sufficiently thin to allow the edges to be moved between the body of the tick and the animal's skin.

It is preferred that the notch be about three-quarters of an inch to about one and one-half inch long and the width of the opening of the notch be about one-quarter to about one-half inch long. It is further preferred that the device be of a length of about three to about five inches long. It is also preferred that the device further include means to catch and hold a tick removed with the device. It is further preferred that a tick means a patch of high sliding friction, including a sticky surface such as contact adhesive, located immediately to the rear of the notch point to temporarily hold the dislodged tick. It is further preferred that said means include that the front section further include a bottom wall with side walls and a rear wall extending upwardly from the bottom wall to form a cup shape partially surrounding the point of the notch. This means with the cup can also include the patch of high sliding friction in the cup shape.

Another aspect of the invention is a method for removing ticks that have penetrated an animal's skin. The method includes providing a tick removing device as described herein above. The method then includes grasping the rear end section of the device and placing the bottom face of the front end section against the person's skin proximate the tick with the wide section opening of the notch pointed at the tick. The method then includes sliding the device toward the tick until the side edges of the notch contact the tick, and continuing a slight forward pressure sliding the device forwardly lifting the tick out of the skin. It is generally not necessary to exert any downward pressure to pry the tick out as it will "let go" and be available for disposal.

DESCRIPTION OF PREFERRED EMBODIMENTS

Figure 1:
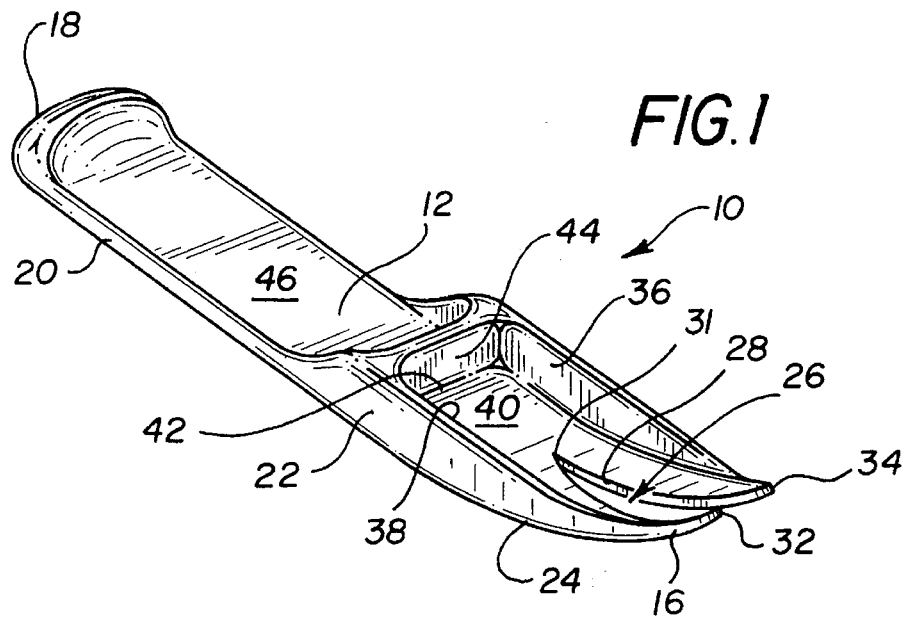
FIG. 1 is a top, front, left side perspective view of a tick removing device of the invention.
Figure 2:
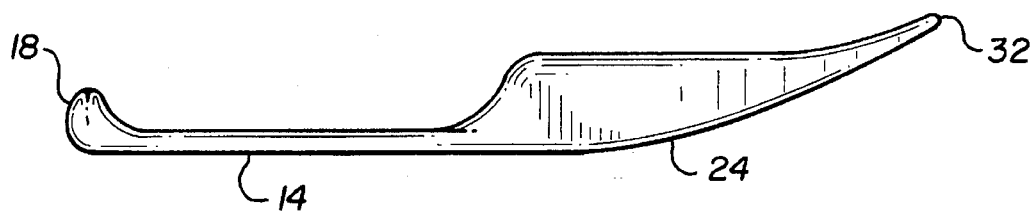
FIG. 2 is a left side plan view thereof, the right side plan view being a mirror image thereof.
Figure 3:
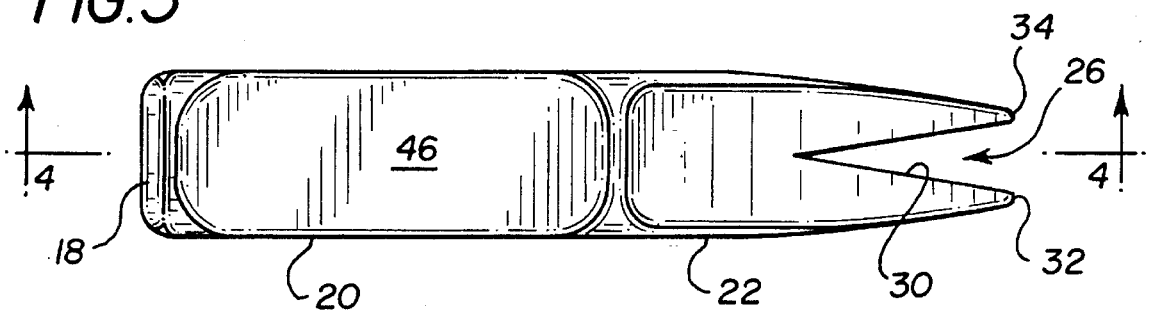
FIG. 3 is a top plan view thereof, the bottom view thereof being identical except that the bottom surface is essentially flat in the rear and curving upwardly in the front with no hidden configurations.
Figure 4:
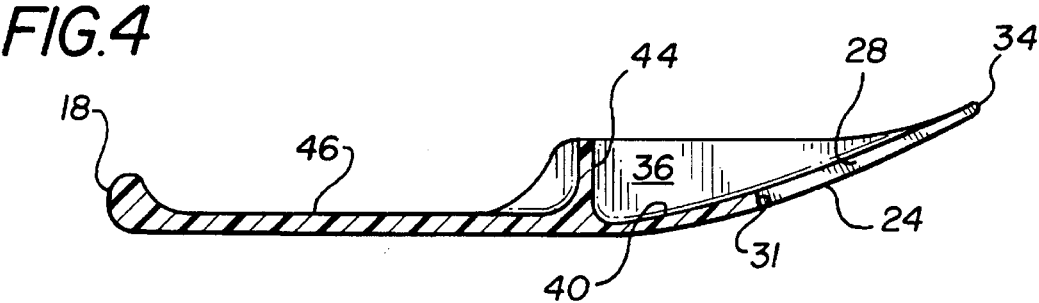
FIG. 4 is a cross-sectional side view taken along lines 4—4 of FIG. 3.
Figure 5:
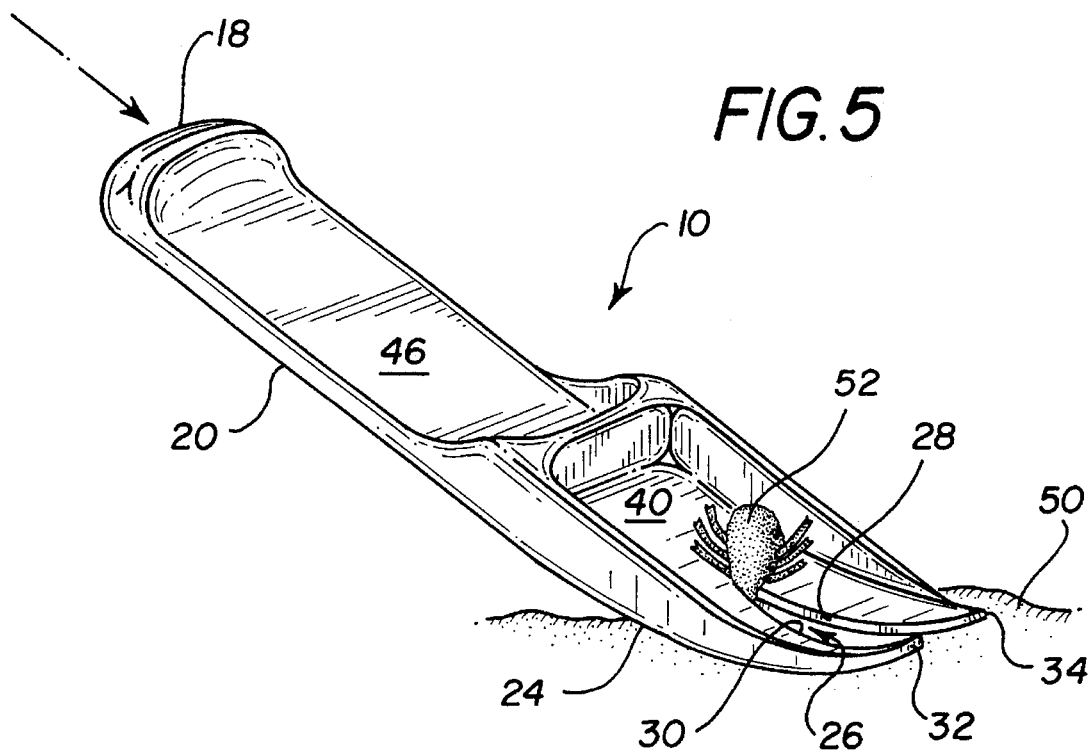
FIG. 5 is a perspective view of the device showing it being slid under a tick imbedded in an animal's skin.
Figure 5A:
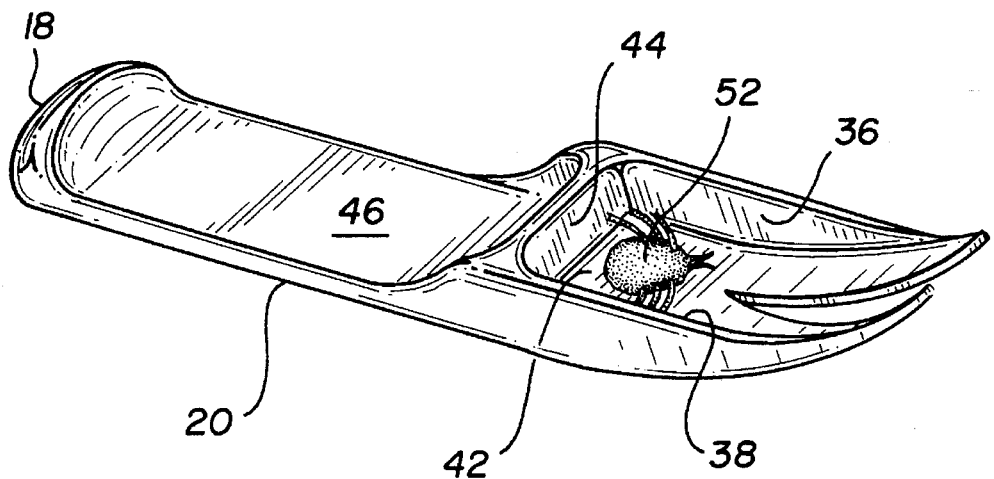
FIG. 5A is a similar view thereof after the tick has been lifted free.

Device 10 is illustrated in FIGS. 1 through 4 and shown in use in FIGS. 5 and 5A. Device 10 is injected molded of a thermoplastic polymer which may be rigid or semi-rigid and includes polyolefins, such as polypropylene, polyethylene and the like, ABS, polystyrene, polymethyl methacrylate, polycarbonate, and engineering plastics such as DELRIN®, nylon, and the like. The device is about four inches long and about one inch wide. Device 10 has top 12, an essentially flat planar rear surface 14, and bottom front section surface 24 which is angled upwardly from a rocking pivot point located about two inches rearwardly of front 32. Device 10 terminates at front end 16 and rear end 18 and consists of rear end section 20 and front end section 22. Device 10 is grasped in the hand holding rear end section 20 with a thumb resting on top panel surface section 46. A "V"-shaped notch 26 is cut into front end 16 and is bounded by right side notch edge 28 and left side notch edge 30. These edges are about 1/64 to about 1/32 inch thick or even thinner. With notch 26 cut out, front end 16 terminates at left blunt front point 32 and right blunt front point 34. A cup shape is formed behind notch point 31 by right side wall 36, left side wall 38 and rear wall 44 all extending upwardly from bottom surface 40 of the bottom panel section. The angled upwardly front section provides an incline and an effective fourth side of cup 42. As shown in FIG. 5, device 10 has been slid along skin 50 with the opening of notch 26 being aimed at tick 52. The device is slid toward and ultimately under tick 52 until the base edges of notch 26, close to point 31 of the notch, rest against the neck of the tick. Device 10 is then gently slid forwardly against tick 52, as shown in FIG. 5, lifting tick 52 out of skin 50. As shown in FIG. 5A, tick 52 is caught in cup 42 so that it may be easily carried to a place of disposal. It is preferred that bottom surface 24 angle upwardly from a location rearward of point 31 of notch 26. Although face 24 is shown curved, that surface may be flat so long as it angles upwardly from the plane of bottom surface 14. In device 10, front bottom surface 24 is angled upwardly at about twenty degrees. That angle may easily be thirty degrees or greater and still be quite effective. Notch 26 is about one and three eighths inch long from opening to point 31 and is about three eighths inch wide at ends 32 and 34. A pivot point where surface 24 angles upwardly is about two and one quarter inches from the front end.

Figure 6:
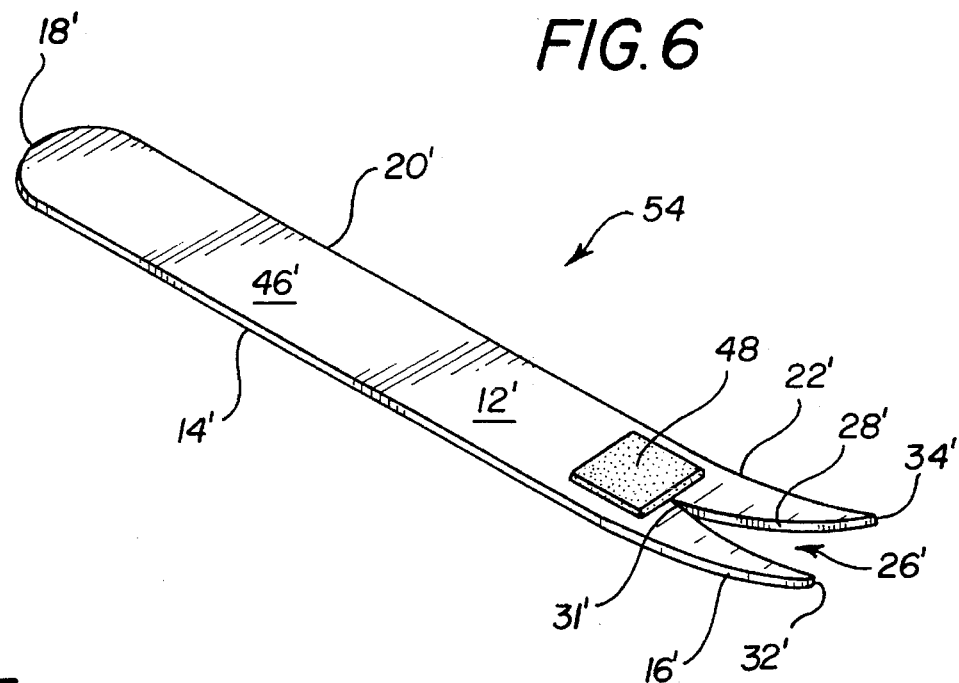
FIG. 6 is a front, top, left side perspective view of a second embodiment of the invention.
Figure 7:
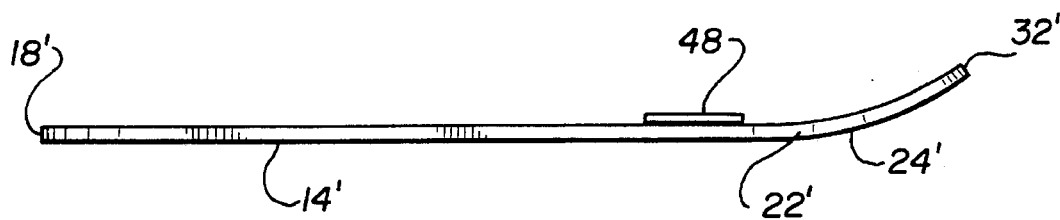
FIG. 7 is a left side plan view thereof, the right side being a mirror image thereof.
Figure 8:
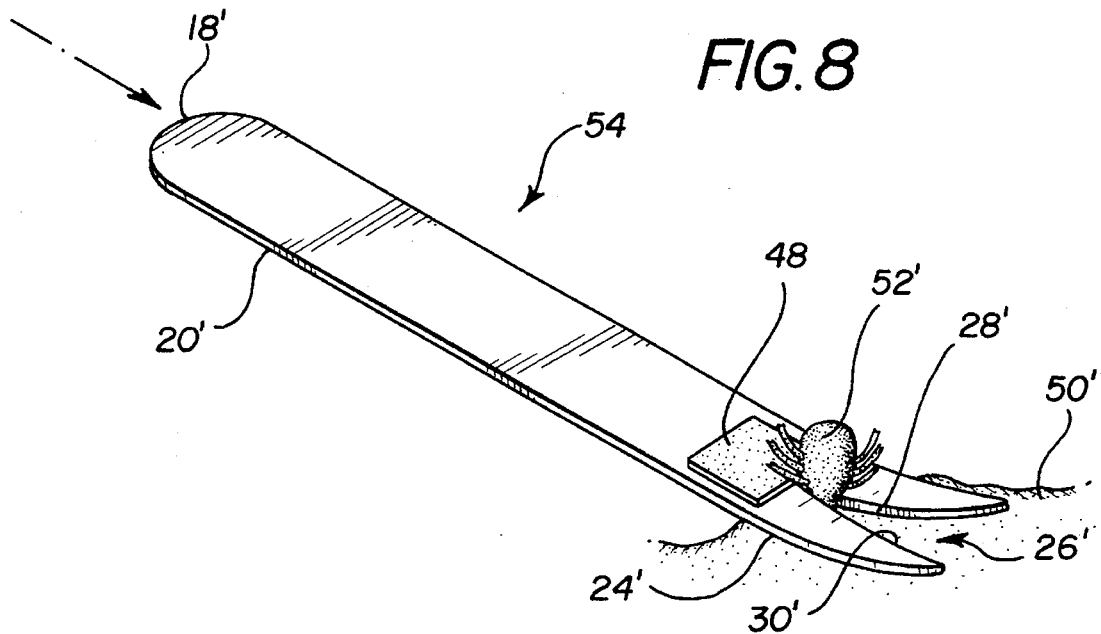
FIG. 8 is a perspective view of said device shown being inserted under a tick imbedded in the skin.

Device 54 is illustrated in FIGS. 6 through 7 and shown in use in FIG. 8. Device 54 is constructed of steel sheet about twenty to forty mils thick. Parts and sections of device 54 and for 52 that are similar to that illustrated in FIGS. 1 through 5 are designated with a prime on identifying numbers in FIGS. 6 through 8. In device 54 notch 26' is slightly less than one inch in length, about three eighths inch wide. Device 54 is about five inches long. It is preferred that the width of the notch be about one quarter inch to about one half inch wide and about three quarters inch to about one and one half inches long. The overall length of the device can range down to about three inches long or even smaller and any length bigger than about five inches is not necessary. In device 54 front section 22' angles upwardly at about fifteen degrees at or just slightly to the rear of point 31' of notch 26'. For best results, this start of the upward angle should be at or to the rear of the point of the notch. As illustrated in FIG. 8, device 54 is used in a similar fashion as that of device 10 wherein notch 26' is slid along skin 50' until edges 28' and 30' abut the neck of tick 52'. Device 10 is gently pressed against the body of the tick to lift the tick 52' out of the skin. Two sided contact adhesive patch 48 is positioned on surface 12' immediately to the rear of point 31' to catch or at least make carrying tick 52' to disposal. If storage of an even smaller device is desired, a hinge break may be provided transverse across the rear end section 20' of device 54 allowing the rear section to be folded to abut the bottom surface of front section 22'. Metal devices of this invention may be up to about one sixteenth inch to about one eighth inch thick, but it is preferred that side edges 28' and 30' of the notch be relatively thin close to the edges to more easily allow the device to be slid under and against the neck of the tick. The device may be constructed of a lightweight metal, such as aluminum or the like and the thickness of the device at any location will depend upon the rigidity of the material used for construction. The device may be supplied with a pouch for protection and/or attachment to a belt or other portion of a person's clothing. It may stored in a combination holder similar to those used to attach a knife to a person's belt.

While this invention has been described with reference to specific embodiments disclosed herein, it is not confined to the details set forth and the patent is intended to include modifications and changes which may come within and extend from the following claims.

I claim:

1. A tick removing device to lift off ticks that have penetrated an animal's skin, the device comprising an integral elongate body comprising:

(a) a top, bottom, a front end, and a rear end, (b) a rear end section shaped to be grasped in a hand of a person, (c) a front end section comprising:

(i) a "V" shaped notch cut into the front end with a point of the notch extending towards the rear end and a wide portion of the notch opening through the front end, (ii) an upper surface rearwardly of the point of the notch, (iii) a bottom face of a bottom wall angled frontwardly and upwardly from a location at or rearwardly of the point of the notch, and (iv) side edges of the notch proximate the point of the notch being sufficiently thin to allow the edges to be moved between the body of the tick and the animal's skin, and (d) holding means to hold the tick on the device comprising a high sliding friction section of contact adhesive located on said upper surface, the level of friction being sufficient to prevent the tick from sliding off the device.

2. The device of claim 1 wherein the notch is about three-quarters of an inch to about one and one-half inches long.

3. The device of claim 2 wherein a width of the opening of the notch is about one-quarter to about one-half inch long.

4. The device of claim 1 of a length of about three to about five inches long.

5. The device of claim 1 wherein the holding means further comprises side walls and a rear wall extending upwardly from the bottom wall to form a cup shape.

6. The device of claim 5 wherein the high sliding friction section is located on the upper surface within the cup shape.

7. The device of claim 5 wherein the device is an integral molding of a thermoplastic polymer.

8. A method for removing ticks that have penetrated a animal's skin, the method comprising:

(A) providing a tick removing device comprising an integral elongate body comprising:

(i) a top, bottom, a front end, and a rear end, (ii) a rear end section shaped to be grasped in a hand of a person, (iii) a front end section comprising:

(a) a "V" shaped notch cut into the front end with a point of the notch extending towards the rear end and a wide portion of the notch opening through the front end, (b) an upper surface rearwardly of the point of the notch, (c) a bottom face of a bottom wall angled frontwardly and upwardly from a location at or rearwardly of the point of the notch, and (d) side edges of the notch proximate the point of the notch being sufficiently thin to allow the edges to be moved between the body of the tick and the animal's skin, and (iv) holding means to hold the tick on the device comprising:

(a) side walls and a rear wall extending upwardly from the bottom wall to form a cup shape, and (b) a high sliding friction section located on said upper surface, the level of friction being sufficient to prevent the tick from sliding off the device, (B) grasping the rear end section of the device, (C) placing the bottom face of the front end section against the animal's skin proximate the tick with the wide portion of the notch pointed at the tick, (D) sliding the device toward the tick until the side edges of the notch contact the tick, and (E) continuing to slide the edges of the notch against the tick lifting the tick out of the skin and hold the tick on the holding means.

9. A tick removing device to lift off ticks that have penetrated an animal's skin, the device comprising an integral elongate body comprising:

(a) a top, bottom, a front end, and a rear end, (b) a rear end section shaped to be grasped in a hand of a person, (c) a front end section comprising:

(i) a "V" shaped notch cut into the front end with a point of the notch extending towards the rear end and a wide portion of the notch opening through the front end, (ii) an upper surface rearwardly of the point of the notch, (iii) a bottom face of a bottom wall angled frontwardly and upwardly from a location at or rearwardly of the point of the notch, and (iv) side edges of the notch proximate the point of the notch being sufficiently thin to allow the edges to be moved between the body of the tick and the animal's skin, and (d) holding means comprising:

(i) side walls and a rear wall extending upwardly from the bottom wall to form a cup shape, and (ii) a high sliding friction section located on said upper surface, the level of friction being sufficient to prevent the tick from sliding off the device.

10. The device of claim 9 wherein the high sliding friction section is contact adhesive.

11. The device of claim 9 wherein the device is an integral molding of a thermoplastic polymer.

* * * * *